US011980715B2

(12) United States Patent
Shah et al.

(10) Patent No.: US 11,980,715 B2
(45) Date of Patent: May 14, 2024

(54) ENDOTRACHEAL INTUBATION ASSISTANCE SYSTEM

(71) Applicants: Amit N. Shah, North Potomac, MD (US); Curt S. Kothera, Rockville, MD (US); Gregory J. Hiemenz, Silver Spring, MD (US)

(72) Inventors: Amit N. Shah, North Potomac, MD (US); Curt S. Kothera, Rockville, MD (US); Gregory J. Hiemenz, Silver Spring, MD (US)

(73) Assignee: InnoVital, LLC, Calverton, MD (US)

( * ) Notice: Subject to any disclaimer, the term of this patent is extended or adjusted under 35 U.S.C. 154(b) by 41 days.

(21) Appl. No.: 17/505,055

(22) Filed: Oct. 19, 2021

(65) Prior Publication Data

US 2022/0118207 A1 Apr. 21, 2022

Related U.S. Application Data

(60) Provisional application No. 63/094,081, filed on Oct. 20, 2020.

(51) Int. Cl.
| | | |
|---|---|---|
| *A61B 1/00* | (2006.01) | |
| *A61B 1/005* | (2006.01) | |
| *A61B 1/06* | (2006.01) | |
| *A61B 1/267* | (2006.01) | |
| *A61M 16/04* | (2006.01) | |

(52) U.S. Cl.
CPC ..... *A61M 16/0488* (2013.01); *A61B 1/00006* (2013.01); *A61B 1/00154* (2013.01); *A61B 1/0052* (2013.01); *A61B 1/0661* (2013.01); *A61B 1/267* (2013.01); *A61M 2205/0233* (2013.01)

(58) Field of Classification Search
CPC ...... A61M 16/0488; A61M 2205/0233; A61B 1/00006; A61B 1/00154; A61B 1/0052; A61B 1/0661; A61B 1/267
USPC ....................................................... 600/120
See application file for complete search history.

(56) References Cited

U.S. PATENT DOCUMENTS

| | | | |
|---|---|---|---|
| 6,918,388 B2 * | 7/2005 | Brain | A61M 16/04 128/207.15 |
| 8,746,239 B2 | 6/2014 | Yoshida | |
| 10,456,025 B2 | 10/2019 | Hung et al. | |
| 2002/0071287 A1 * | 6/2002 | Haase | G02B 27/20 D26/37 |
| 2007/0225560 A1 * | 9/2007 | Avni | A61B 1/000095 600/118 |
| 2008/0017195 A1 * | 1/2008 | Yoshida | A61M 16/0418 128/200.26 |
| 2013/0041227 A1 | 2/2013 | Chan et al. | |

(Continued)

*Primary Examiner* — Timothy J Neal
*Assistant Examiner* — James Edward Boice
(74) *Attorney, Agent, or Firm* — Steven Scott Lloyd; Gordon Feinblatt LLC (57) ABSTRACT

A handheld system that is used with an endotracheal tube to facilitate endotracheal intubation is disclosed. The device includes a lighted bougie and an intubating channel, a handle, at least one sensor, a midline alignment light, a tongue grasper, a power source, and electronics. These components combine to form an integrated airway management system. During operation of the system, the light transilluminates the anterior neck tissue of the patient and glows brightly in the midline when the bougie is placed in the trachea.

26 Claims, 8 Drawing Sheets

(56) References Cited

U.S. PATENT DOCUMENTS

| | | | | |
|---|---|---|---|---|
| 2013/0317300 | A1* | 11/2013 | Berci | A61B 1/042 600/188 |
| 2014/0179998 | A1* | 6/2014 | Pacey | A61B 17/0218 600/210 |
| 2015/0173598 | A1* | 6/2015 | Alexander | A61B 1/00154 600/187 |
| 2015/0290414 | A1* | 10/2015 | Vasan | A61B 1/3132 128/200.26 |
| 2016/0081539 | A1* | 3/2016 | Pagan | A61B 1/00154 600/184 |
| 2019/0142262 | A1* | 5/2019 | Inglis | A61B 1/00124 600/188 |

\* cited by examiner

ENDOTRACHEAL INTUBATION ASSISTANCE SYSTEM

CROSS-REFERENCE TO RELATED APPLICATION(S)

The present application derives priority from U.S. provisional application Ser. No. 63/094,081 filed 20 Oct. 2020.

BACKGROUND OF THE INVENTION

Field of the Invention

The present invention relates to a system for assisting a user in endotracheal intubation of a patient.

Description of the Invention

Endotracheal intubation is an essential resuscitative procedure in the emergency setting. Endotracheal intubation (ETI) is the definitive approach to airway management and is an essential resuscitative procedure in the emergency setting. Despite its prevalence, ETI is a difficult skill to acquire and maintain.

A recent study found that an ETI proficiency rate of 90% demands experience with 75 ETI cases. Resident anesthesia physicians, in fact, are required to perform hundreds of intubations during the course of their training. The American Heart Association recommends that paramedics perform 6-12 intubations per year to maintain proficiency. EMS systems that have reported high ETI success rates require a minimum of 15 ETI's annually. Despite the incorporation of simulation-based training and use of tools such as video laryngoscopy, true ETI proficiency is simply unattainable for many pre-hospital providers. Battlefield conditions present an added layer of complexity, often involving confined spaces, poor patient and/or provider positioning, hostile action, lack of airway visibility, or maxillofacial or neck trauma. Because of these complexities, cricothyroidotomy has become the default battlefield airway management procedure. This surgical approach has historically had high failure rates and significant long-term complications, as well as substantial training and refresher training requirements, however.

Light guided or lightwand intubation enables accurate ETI without the visualization and/or identification of traditional anatomical landmarks. In traditional light guided intubation, a stylet with a distally positioned light is placed inside an endotracheal tube and inserted towards the glottic opening. The stylet serves to add rigidity to the otherwise flexible endotracheal tube and to transilluminate the anterior surface of the neck. The user references the position of the transilluminated light to guide the stylet and endotracheal tube assembly towards and through the vocal cords. Lightwand intubation allows ETI from a variety of operator-patient orientations. The correct use of currently available lightwand products requires significant skill and experience. Moreover, the light source itself is often insufficient for use in higher ambient light conditions and/or patients with anterior neck fat.

The present invention builds upon the significant experience with light-guided or lightwand intubation. The present invention also adds features that aid the operator in appropriate endotracheal tube positioning and that improve light transillumination. The present invention considers both the traditional lighted stylet approach and a lighted bougie approach. In the lighted bougie approach, the bougie—a tube with greater rigidity and smaller diameter than a typical endotracheal tube and with an atraumatic tip—is initially advanced towards and through the vocal cords independent of the endotracheal tube. Improved transillumination from the lighted bougie provides intraprocedural feedback with regard to bougie position relative to the oropharynx, trachea and esophagus, and prompts the user to perform corrective actions in order to achieve endotracheal bougie placement prior to endotracheal tube placement.

SUMMARY OF THE INVENTION

The endotracheal intubation assistance system of the present invention may have a plurality of components including at a minimum a lighted bougie and an intubating channel. Other components that may be part of the system include, but are not limited to, a handle, at least one sensor, a midline alignment light, and a tongue grasper. The system has a power source, and may additionally include electronics. These components combine to form an integrated airway management system that is used with an endotracheal tube. The result is a handheld system that facilitates ETI in normal or difficult airway scenarios employing a stepwise approach. Each system component is summarized below.

The lighted bougie is a flexible introducer with at least one light that blinks near or at the distal end. There are preferably two lights that blink out-of-phase with each other such that only one light is on at a time. There may be a momentary period where both lights are off. The lights are preferably separated an axial distance of at least 1 cm with the distal-most light located within 2.5 cm of the distal tip of the bougie. The color of the light is preferably red or near-infrared wavelengths, such as approximately 625 nm to 2500 nm, with the visible red being preferred for use with the naked eye and the near-infrared being preferred for use with night vision goggles. During operation of the system, the light transilluminates the anterior neck tissue of the patient and glows brightly in the midline when the bougie is placed in the trachea.

In the preferred embodiment, the lighted bougie terminates at its proximal end with an electrical connector that is plugged into the handle to receive the power and signal for activating the light(s). However, an alternate embodiment has a small electronics and power package mounted to the proximal end of the lighted bougie that only docks into the handle to prevent potential flailing of the bougie during use of the system.

The lighted bougie preferably has depth markings along its length to aid the user in appropriate placement and re-positioning during use. Depth markings may include discrete centimeter (or tens of cm) markings, measured from the distal tip, and an alignment marking for where the proximal end of the endotracheal tube will fall when the distal tip of the bougie and endotracheal (ET) tube are aligned.

The lighted bougie preferably has sufficient rigidity to be advanced and/or guided by the user in a controlled fashion, though flexible enough for the user to purposefully alter its shape. Accordingly, the properties of the lighted bougie will facilitate bougie placement inside the trachea and facilitate endotracheal tube advancement and passage into the trachea.

In a preferred embodiment, the means for grasping the intubating channel (e.g., extension/arm of channel itself or separate handle) is a central component of the system. It is preferably: (1) what the user holds when performing the intubation procedure; (2) how the user manipulates the intubating channel and thereby the laryngeal anatomy (including to apply anterior lift); (3) where the user controls are located; (4) where the lighted bougie is plugged in or docked to receive electrical power and/or prevent its proximal end from flailing; and (5) a housing/enclosure for the electronics and power source, including any operational indicators (e.g., "power-on" indicator, "battery needs changed" indicator). This portion of the system may also include a temporary holding slot for the ET tube bag-valve-mask adapter. The term "handle" is herein defined as any means for grasping the intubating channel, whether it be an extension of the channel itself or a separate system component.

A midline alignment light may be projected from the handle onto the patient's anterior neck in order to help the user maintain midline placement of the handle and inserted channel and as an indication to the user as to where to look for the transilluminating bougie light. In the preferred embodiment, a low-power laser pointer (dot) is used and passes through a lens that transforms the point into a vertical (i.e., cephalocaudal) line. This is not meant to be limiting, however, as any such lighted projection could be used for the same purpose without changing the invention, including but not limited to solid line(s), dashed line(s), parallel lines, non-parallel lines, curve(s), and other polygons or shapes. Preferably, the midline light is constantly on as opposed to the blinking bougie light, and the midline light is preferably a different color from the bougie light (e.g., green).

The handle may also be used to project other indicators on the anterior neck and/or chest. The projected indicator light or lights may be used to help remind and/or guide the user in how to hold or orient the handle in the X, Y, and/or Z spatial planes. In one embodiment, the midline, vertical/cephalocaudal line described above may be used along with a dot projected from the top of the handle to provide additional feedback on upward (towards the ceiling) and rocking (handle top towards the toes vs. towards the head) handle displacement.

User controls include a power switch which, when depressed by the user, activates the system. In the preferred embodiment the power switch is an instantaneous trigger that is pulled and held by the user to connect power to the system and released to disconnect power. One embodiment of the system includes a power intensity switch as a user input. In the preferred embodiment the power intensity switch is a three-position rocker switch with a default center position setting that enables selection of a light intensity setting that is appropriate for most patients, though any similar type of switch/user control could be used within the scope and spirit of the invention. Flipping the switch one way from the center position will reduce the light intensity for patients that require dimmer light for optimal transillumination, such as patients with skinny necks and pale skin, or for low ambient light conditions. Flipping the switch the other way will increase the light intensity for patients that require brighter light for optimal transillumination, such as patients with excessive anterior neck tissue and dark skin, or for high ambient light conditions. An alternate embodiment may include a rotating dial or knob as a light intensity adjustment user input. Additional embodiments may include an on/off switch for the midline light and an infrared switch which changes the bougie and/or midline light output to wavelengths that are optimized for night vision goggle visualization.

The intubating channel is preferably a curved tubular structure that is rigid in comparison to the stiffness of the lighted bougie and in comparison to an endotracheal tube. The purpose of the intubating channel is to effectively make rigid the bougie and endotracheal tube over the length in which they preside inside the intubating channel. This temporary rigidity facilitates placement of the more flexible structures at the glottic opening such that they can be delivered into the trachea safely and effectively. The intubating channel therefore serves the purpose of a conventional stylet, but does so exterior to the endotracheal tube instead of interior to it. The external stylet function of the intubating channel may also provide protection to the bougie and endotracheal tube and cuff as they are positioned at the glottic opening, and also may facilitate appropriate placement in the presence of obstructions. The intubating channel preferably attaches to the bottom of the handle in a similar manner as a typical laryngoscope blade attaches to a handle, and is removable, though an alternate embodiment has the channel fixed to the handle. In the fixed configuration, the intubating channel is preferably pivotable about an axis on the bottom of the handle to make the handle-channel assembly somewhat collapsible to facilitate packaging. The intubating channel is preferably transparent such that depth markings printed on the endotracheal tube can be read through the channel. The intubating channel need not have a solid curved cylindrical body, as some embodiments may have cutout sections in the channel to facilitate the procedure and/or user interactions. The intubating channel, whether completely cylindrical or cylindrical with a cut-out, may serve the additional purpose of a ventilation conduit. As an example, an endotracheal tube adapter may be attached to the proximal portion of the channel and the patient may be bag-ventilated through the intubating channel in a manner that is superior to bag-valve-mask ventilation. The intubating channel may also feature indica to assist the user in performing the procedure. Exemplary indica include circumferential rings spaced apart axially to guide the user through suggested procedural adjustments and an arrow at the anterior distal tip as a visual cue of correct orientation of the lighted bougie. The intubation system may have more than one size and/or shape of intubating channel for different types of patient anatomy.

The electronics control the non-mechanical operations of the system. Such operations may include activating (connecting the power source to the circuitry) the system when the user pulls the activation trigger; blinking the light(s) on the bougie at the prescribed frequency, duty cycle, and phasing; adjusting light intensity (e.g., current) to the light (s) based on the position of a user input (e.g., switch or knob); adjusting light intensity to the light(s) based on the input from a sensor (e.g., ambient light sensor); switching the midline light on/off based on user input; switching to night vision goggle mode per user input; illuminating an indicator that the power is on and the system is functioning correctly; and illuminating an indicator that the power source is sufficient or insufficient to operate the system. Processing, logic, and memory are integral components of the electronics, which are programmed with software to perform the preferred non-mechanical operations of the system. The software programmed into the electronics may also feature safety functions. One such function in the preferred embodiment is that the power indicator and/or midline light may turn off if the lighted bougie becomes unplugged from the power source, even if the user is still depressing the activation trigger.

The power source is preferably a battery. The power source primarily provides electrical power to the bougie to illuminate its distal light(s). Since the bougie lights are preferably blinking out-of-phase with each other (when more than one light is present), the power source also supplies power to the control electronics that produce the pulsing/blinking signal. Any on-board sensors or indicators also receive power from the power source, as does the midline light. There is preferably an access panel in the handle to easily allow changing/charging of the battery. In the embodiment where the power source and electronics are housed at or near the proximal end of the bougie, their enclosure also preferably has an access panel to change/charge the battery. In either scenario, in an embodiment with a rechargeable battery, the handle and/or bougie electronics housing may also contain a connector to charge the battery or the means necessary for wireless battery charging.

One or more sensors may be included in the system. In the preferred embodiment an ambient light sensor takes in the light of the ambient environment in which the intubation procedure is being performed and, in connection with the control logic of the electronics, adjusts the output light intensity of the bougie light(s) and/or midline light intensity. For example, a dimmer light intensity is required in a darker ambient setting, whereas a brighter light intensity is required in a brighter ambient setting to ensure optimal transillumination in the patient. The preferred embodiment uses an ambient light sensor instead of a manual user control to simplify the procedure for the user. That is, with a light sensor, there is one less setting that the user must select prior to beginning the procedure. Note, however, that an alternate embodiment may replace the ambient light sensor (and accompanying automatic control electronics) with a user input, such as a switch or knob, that manually adjusts the brightness level of the bougie lights.

The preferred embodiment of the system will now be described in a typical use case. The user begins by assembling the system. Assembly preferably starts by removing the ET tube adapter and inserting it into the temporary holding slot on the handle and then loading the bougie into the ET tube. The bougie/ET tube assembly is placed into the intubating channel and the distal ends of the bougie and ET tube are aligned such that the tips are at, but generally do not go beyond, the distal end of the intubating channel. The proximal part of the channel is then connected to the distal aspect of the handle and the proximal end of the bougie is connected to the proximal part of the handle. The entire assembly is then picked up, pointed away from the user's eyes, and the trigger is briefly pulled to ensure that the (e.g., green) midline guidance light and (e.g., red) bougie tip lights illuminate.

The use of the preferred embodiment of the system will now be described. While an ambient light sensor automatically adjusts light intensity of the distal bougie lights and/or midline light based on ambient light intensity, the user further selects an appropriate bougie light intensity based on skin color and anterior neck fat. Next, and if necessary, the tongue is pulled out with the tongue grasper so that the tip of the tongue is hanging out of the mouth. The intubating channel, containing the distally aligned bougie/ET tube assembly, is fully inserted into the patient's open mouth. The trigger is pulled and the midline light is aligned with the patient's sternum. Anterior lift is applied with the handle and the bougie is slowly advanced into the patient. The user looks for (e.g., two sequentially) blinking, red bougie light (s) transilluminating in the midline of the patient's neck, along the external green midline light line. Once the blinking red lights have been visualized passing behind the sternum, advancement of the bougie stops. The ET tube is then advanced to an appropriate depth and the ET tube cuff is inflated with a syringe. The proximal end of the bougie is then disconnected from the handle and, while holding the ET tube in position, the bougie is withdrawn from the ET tube and channel. Next, while holding the ET tube in position, the channel is withdrawn from the mouth. The ET tube adapter is removed from the handle holding slot and placed on the proximal end of the ET tube and the patient is ventilated and the ET tube is secured.

Note that the intubating channel may have a cutout section to facilitate ET tube stabilization during withdrawal of the channel. In another embodiment, the tongue grasper may be sized and shaped to fit inside the proximal opening of the intubating channel to likewise stabilize the inserted position of the endotracheal tube during channel withdrawal.

Should one or both blinking bougie lights not be visualized in the midline, appear very faint, or are visualized off midline, the trigger is released and the bougie is withdrawn to the starting position where an indicator line on the bougie is visible just outside (proximal to) the intubating channel, next to the proximal end of the ET tube. The intubating channel is then withdrawn by one indicator marking. The trigger is pulled again, anterior lift is reapplied, and the bougie is again advanced while looking for the blinking red bougie light(s) in the midline along the green line. If the lights are still not prominently visible in the midline, the bougie is again withdrawn to the starting position and the intubating channel is withdrawn by one more (e.g., black) indicator marking. The Bougie is re-advanced as above.

DETAILED DESCRIPTION OF THE PREFERRED EMBODIMENTS

What follows is a description of a preferred embodiment of a system that facilitates endotracheal intubation with light guidance. The exemplary application of the present invention has more than the minimum components and features, but not all that could be considered part of the invention. One skilled in the art will appreciate the additions, subtractions, and variants of components and/or features of the system that are within the scope and spirit of this invention.

Figure 1:
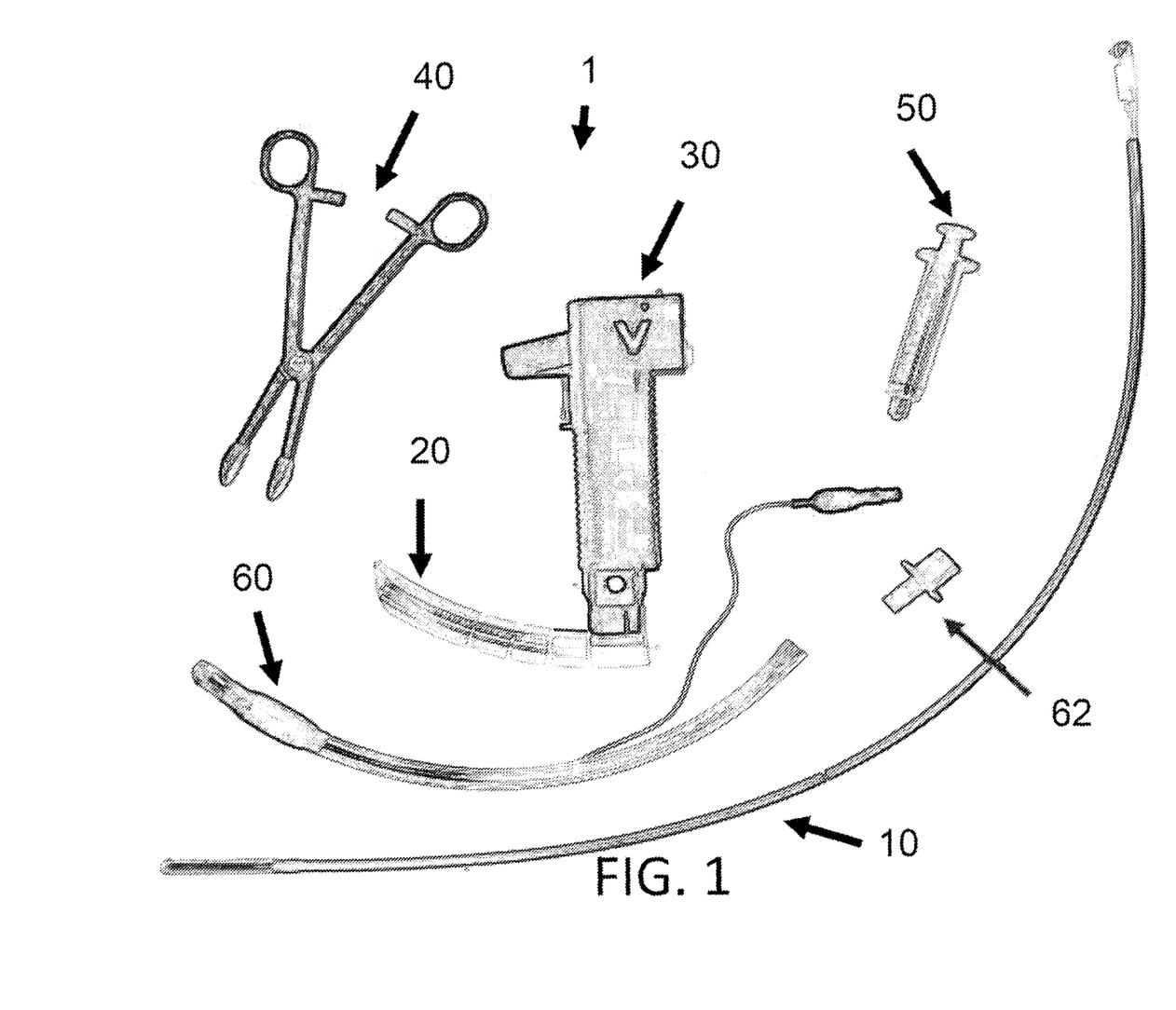
FIG. 1 depicts a photograph of an exemplary endotracheal intubation assistance system of the present invention—not assembled.
Figure 2:
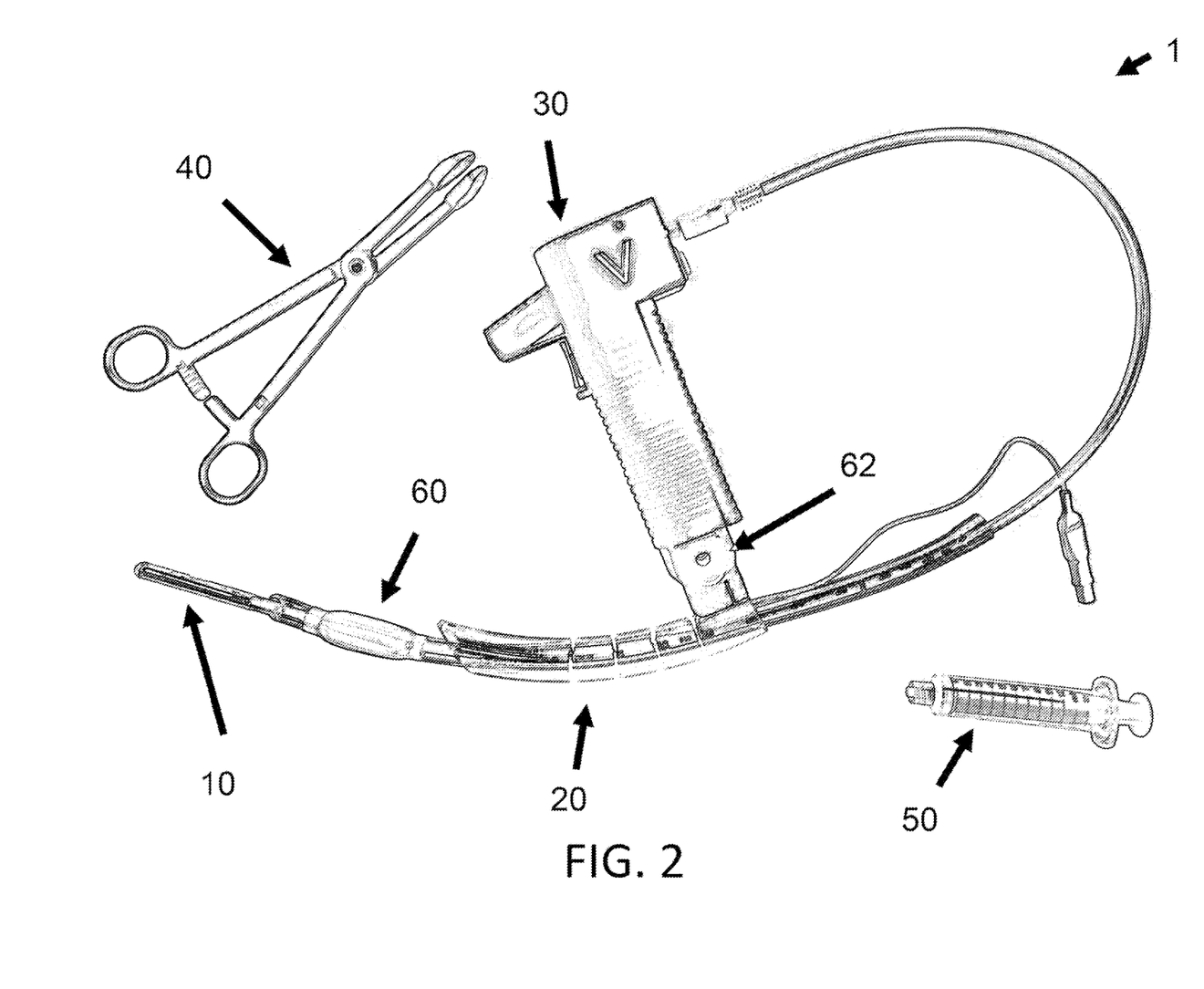
FIG. 2 depicts a photograph of an exemplary endotracheal intubation assistance system of the present invention—assembled.
Figure 3:
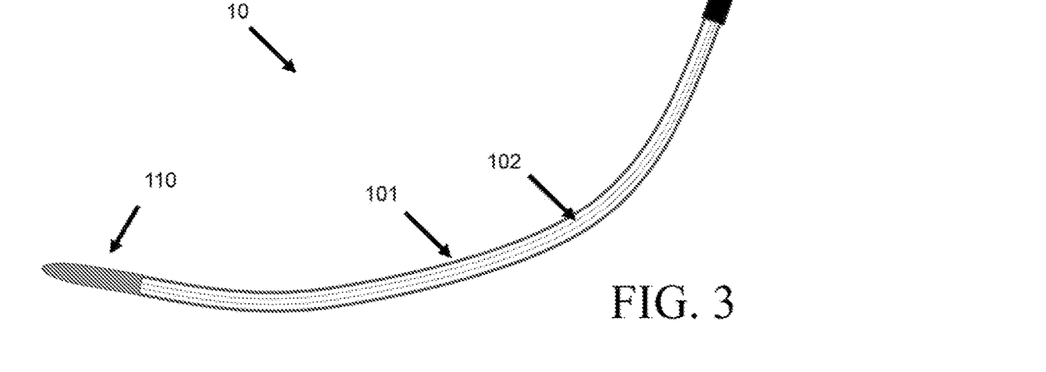
FIG. 3 is a detailed side view of the lighted bougie 10 of FIGS. 1-2.

With reference to FIG. 1-2, the preferred embodiment of the present invention for endotracheal intubation assistance system 1 has six components: lighted bougie 10, intubating channel 20, handle 30, tongue grasper 40, syringe 50, and endotracheal tube 60 with adapter 62. FIG. 1 shows a mostly separated view of the components, except that intubating channel 20 is attached to the bottom of handle 30. FIG. 2 shows a view of the components assembled and ready for a procedure. Here it is seen that lighted bougie 10 passes internally through endotracheal tube 60, which passes internally through intubating channel 20, which is attached at the bottom of handle 30. Note that the proximal end of lighted bougie 10 is plugged into handle 30, endotracheal tube adapter 62 is stored near the bottom of handle 30, and both tongue grasper 40 and syringe 50 are separate and free from the primary assembly. As shown in FIG. 3, lighted bougie 10 has a flexible body 101 that is generally cylindrical and hollow, such that conductors 102 can pass therethrough to connect distal end 110 to proximal end 130. Alternate embodiments may have conductors 102 embedded within the material of flexible body 101, either with or without it being hollow. Bougie distal end 110 contains the light(s) (e.g., light emitting diode) and any mounting parts. Bougie proximal end 130 preferably terminates in an electrical plug.

Figure 4:
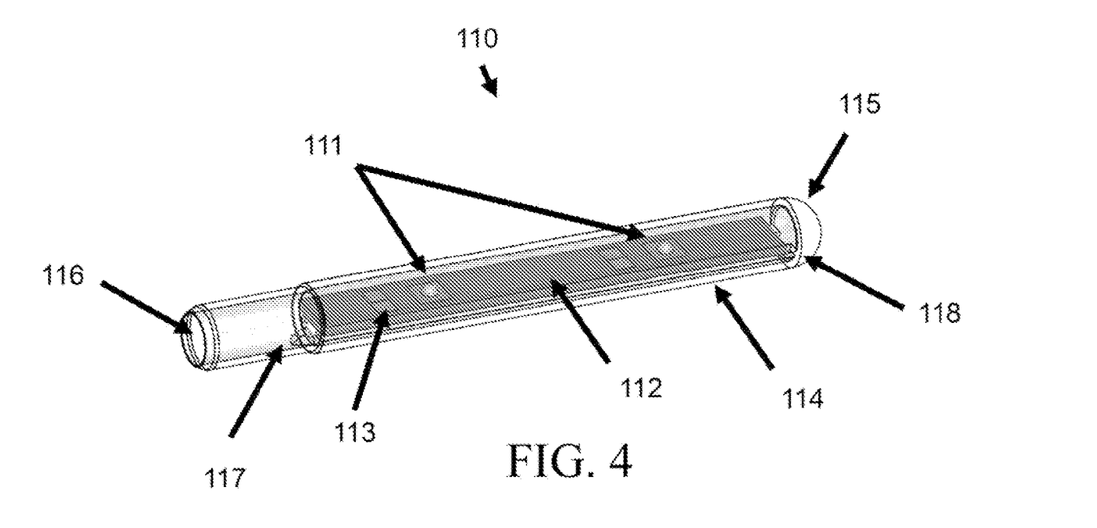
FIG. 4 is a close-up view of an embodiment of bougie distal end 110.
Figure 5:
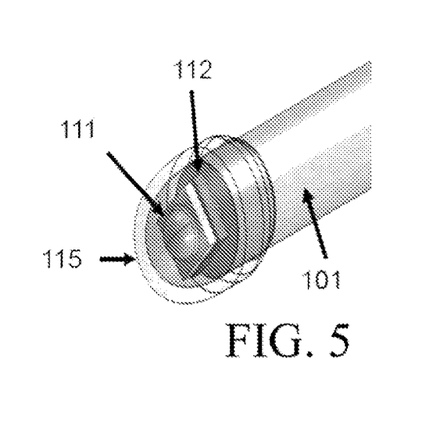
FIG. 5 is a close-up view of another embodiment of bougie distal end 110.

FIG. 4 shows a close-up view of lighted bougie distal end 110. This embodiment has two lights 111 spaced apart from one another and mounted on a printed circuit board 112. The board 112 may have contacts 113 for attaching conductors 102 that pass through flexible body 101 and supply operational power to lights 111, and board 112 may have advanced heat dissipation properties depending on the power requirements and operational duty cycle of lights 111. These electrical components are preferably housed in an at least partially transparent shell 114 with atraumatic distal tip 115 and an opening 116 at the proximal end to attach to flexible body 101. In this embodiment, lights 111 are mounted on top of board 112 such that when in the tube of the patient's trachea, the brightest light intensity is directed anteriorly toward the front of the patient's neck. To maintain this anterior light orientation, there may be a clocking feature 117 that mates to a similar/opposite feature in the distal end of flexible body 101. Shell 114 may also have orientation features, such as shelf 118 upon which board 112 rests to further ensure correct light orientation. In this scenario, proximal plug 130 can only be plugged into handle 30 in one orientation, as well, to ensure correct light directionality. Note that lights 111 may be different wavelengths and may be either co-located or separated depending on the needs of the embodiment. In an alternate embodiment, FIG. 5 shows a light 111 mounted to a board 112 and oriented axially with reference to flexible body 101.

Figure 6:
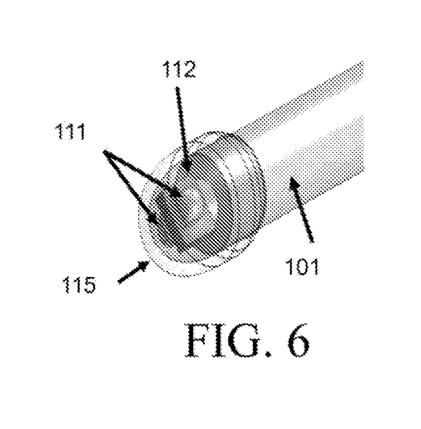
FIG. 6 is a close-up view of another embodiment of bougie distal end 110.

FIG. 6 shows another alternate embodiment where lights 111 are oriented radially with respect to flexible body 101, but on opposing sides of board 112.

Figure 7:
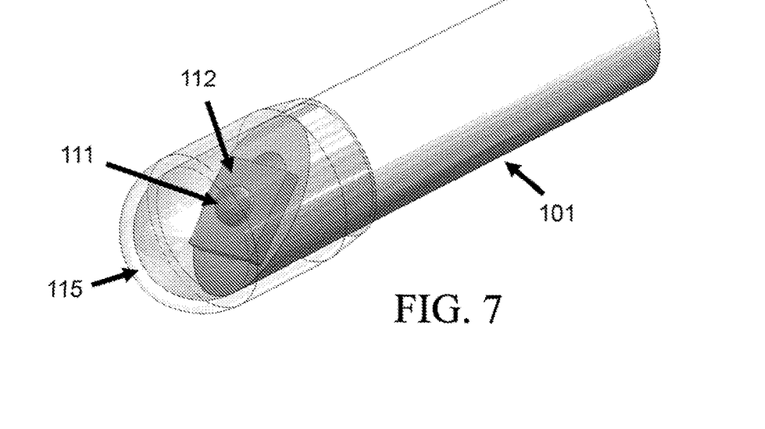
FIG. 7 is a close-up view of another embodiment of bougie distal end 110.

In yet another alternate embodiment, FIG. 7 shows a version of bougie distal end 110, wherein the tip of flexible body 101 is angled such that board 112 and light 111 mounted thereupon are oriented at an angle between axial and radial directions. This embodiment may allow only a single light 111 to be used with reasonable luminous directionality both anteriorly and axially (e.g., down the trachea) for certain cases. The angle could be optimized given specific output ratings of the light 111 being used.

Figure 8:
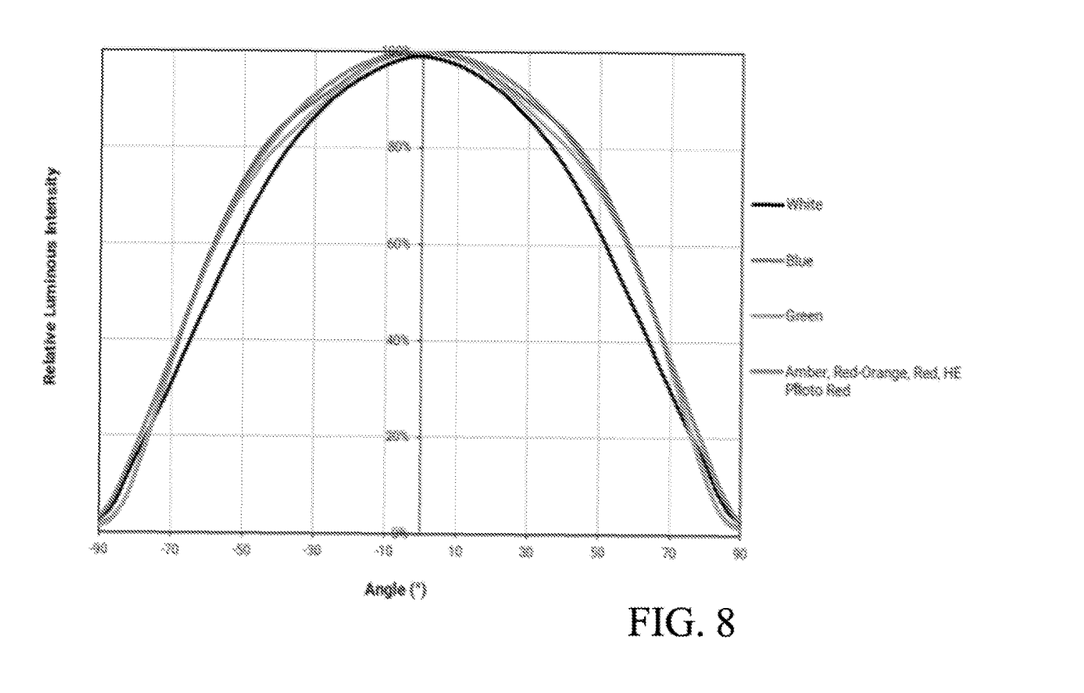
FIG. 8 is a graph of luminous intensity versus angle for light 111.

FIG. 8 shows exemplary curves of luminous intensity versus angle for a light 111, and it can be seen that the exemplary light has intensity of 80% or more over about a 90 deg arc with maximum intensity at 0 deg (+/−45 deg). In this case, light 111 would preferably be mounted on a plane at 45 deg (e.g., halfway between axial and radial) to have maximum transillumination potential over the range of anteriorly to caudally through the trachea. Other angles and preferred light intensities could be used within the spirit and scope of the invention, however. While the preferred embodiment has the power source and any accompanying electronics housed for lighted bougie 10 housed in handle 30, such that lighted bougie 10 can be cheaper and disposable, an alternate embodiment may have the power source and any accompanying electronics housed at the proximal end of lighted bougie 130 in place of the preferred plug.

Figure 9:
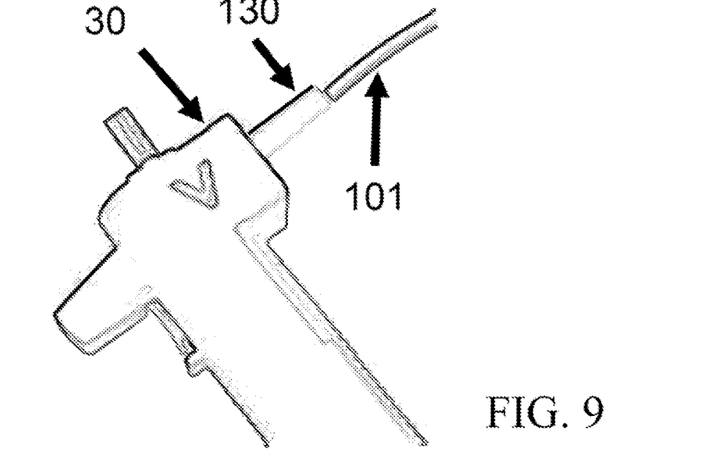
FIG. 9 shows the bougie proximal end 130 configured as a plug for handle 30.

FIG. 9 shows the preferred embodiment with bougie proximal end 130 being a plug for handle 30.

Figure 10:
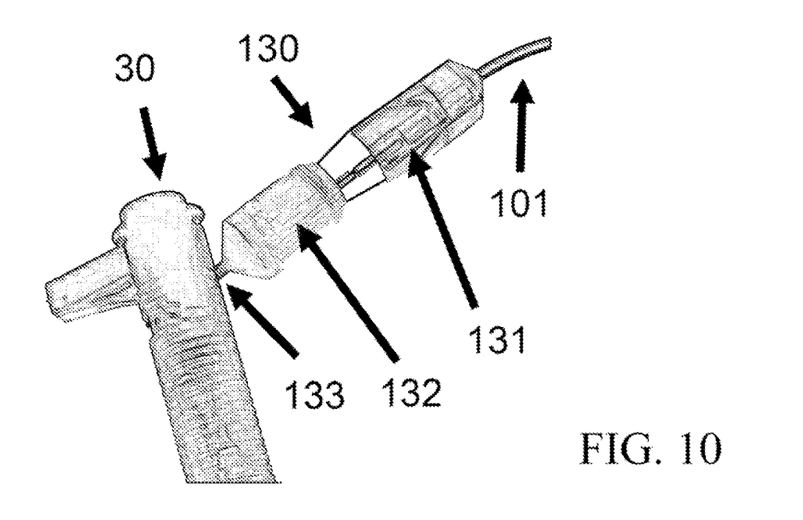
FIG. 10 shows an alternate embodiment of bougie proximal end 130 configured to dock with handle 30.
Figure 11:
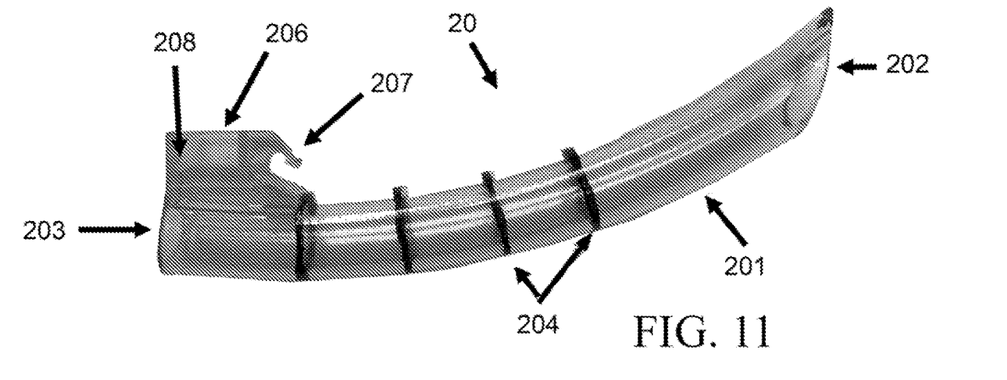
FIG. 11 shows an intubating channel 20 according to an embodiment.

FIG. 10 shows an alternate embodiment where bougie proximal end 130 houses the power 131 (e.g., batteries) and electronics 132, and docks with handle 30 using connector 133. Intubating channel 20 of the preferred embodiment is shown in FIG. 11. The main body 201 is generally a transparent, curved, tubular structure that is open at both ends. Distal opening 202 preferably has an angle where the anterior-most side is longest and posterior-most side is shortest, which could be said to have a posteriorly directed opening. Proximal opening 203 is generally perpendicular to the local curvature of main body 201, but could be angled in any direction if desired. Main body 201 preferably has indica 204 along at least a portion of its length to allow the user to gauge relative depth within the patient's mouth. Main body 201 also preferably has a mounting section 206 for attachment to handle 30. In the preferred embodiment shown, mounting section 206 is on the anterior surface of main body 201 and located near proximal opening 203, though this positioning is not meant to be limiting. To ensure familiarity with users, the attachment of intubating channel 20 to handle 30 is preferably, but need not be, similar to conventional laryngoscope blades to handles. That is, mounting section 206 has a hook 207 at its distal end and detents 208 closer to its proximal end. One skilled in the art will appreciate that other suitable attachments fall within the scope and spirit of the invention. The curvature of intubating channel 20 is preferably of a constant radius and anteriorly biased, which is different than conventional laryngoscopes, but facilitates injection molding manufacture with one or two curved core pins. The preferred range for radii of curvature is from 10-30 cm for intubating channel 20. If two (curved) core pins are used, it may also be possible for intubating channel 20 to have two different radii of curvature along its length. In an embodiment with two different radii of curvature, one of said radii may approach infinity, as it may be desired to have an intubating channel 20 with a straight section. The inner diameter of intubating channel is preferably large enough such that up to an 8.0 endotracheal tube can pass easily therethrough, possibly with the addition of lubrication, but not requiring so. The inner diameter is hence preferably in the range of 1-2 cm for an intubating channel 20 intended for use in adult patients. Smaller variants may be available to smaller patients, such as pediatrics, within the spirit and scope of the invention. The material used for intubating channel 20 is preferably a rigid material, such as polycarbonate, but this is not meant to be limiting, as other materials could easily be used. For example, an alternate embodiment may use a malleable material, such as aluminum, which would provide the user at least some ability to change the curvature of intubating channel 20 to more optimally match the specific needs of a clinical scenario. Use of such a material for intubating channel 20 may reduce transparency, however. This may be acceptable in some cases, but for those where it is not, another embodiment of intubating channel 20 may have at least two materials in its construction, with at least one material being rigid and at least one material being malleable. Preferably the rigid material would have the most transparency and the malleable material would have the least transparency.

Figure 12:
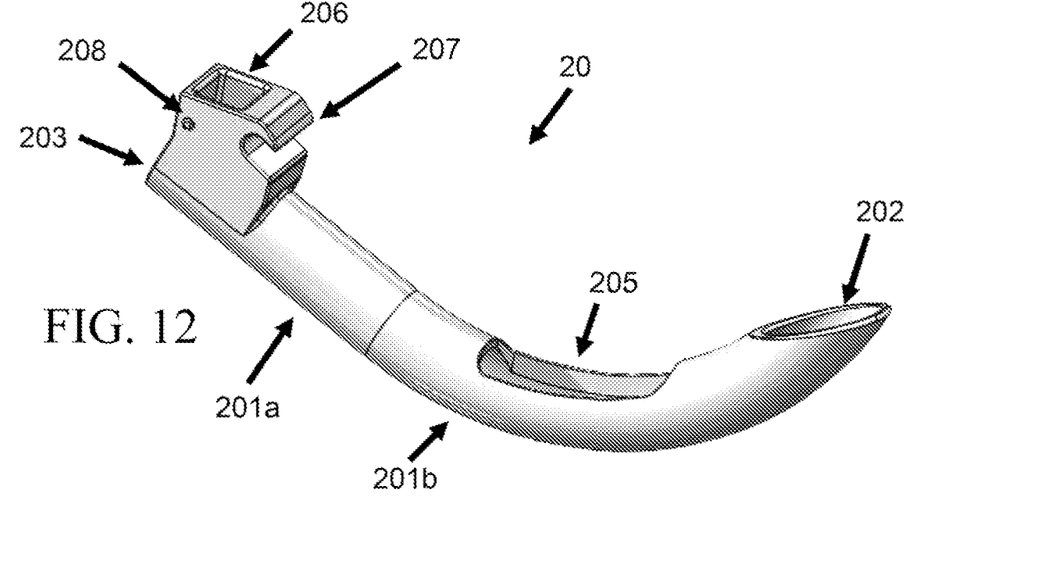
FIG. 12 shows an intubating channel 20 according to another embodiment.

In an alternate embodiment, FIG. 12 shows that intubating channel 20 may have a main body 201 with both a straight section 201a and curved section 201b (e.g., two different radii of curvature). While the figure shows curved section 201b distal to straight section 201a, this is not meant to be limiting and could similarly be flipped. Distal opening 202 may also have a different opening angle. Note that while FIG. 11 showed a posterior opening, FIG. 12 shows an anterior opening, where the posterior-most side is longer than the anterior-most side. No angle (i.e., perpendicular) could also be used within the same invention. Main body 201 may also have a cutout 205 somewhere along its length to allow the user access to the endotracheal tube while it is positioned inside intubating channel 20. Note that in the alternate embodiment with more than one material mentioned above, the straight section 201a here could be rigid and transparent while the curved section 201b could be malleable and opaque, as an example.

Figure 13:
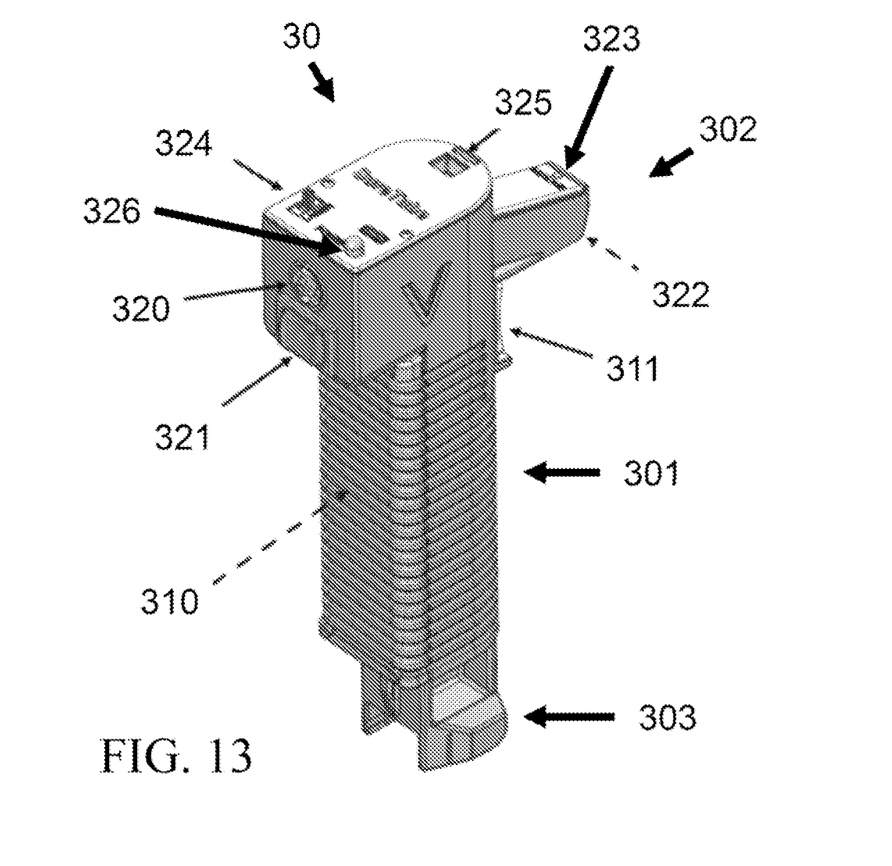
FIG. 13 shows handle 30 according to an embodiment.

FIG. 12 shows cutout 205 on the anterior side and near the distal end, but this is not limiting. It is noted that cutout 205 would reduce the effectiveness of using intubating channel 20 as a ventilation conduit, as discussed above. In yet another alternate embodiment, mounting section 206 may be extended and/or otherwise shaped to provide the function of a handle itself, in addition to or instead of handle 30 (described below). Handle 30 of the preferred embodiment is shown in FIG. 13. Handle 30 includes three sections: elongate body 301, a top 302, and a bottom 303, though the groupings of features need not be limited to the sections as discussed. Elongate body 301 preferably contains the power source 310 (e.g., battery), which may be replaceable or rechargeable, with recharging occurring either outside of handle 30 or inside handle 30, through wired or wireless means. Activation trigger 311 is located on elongate body 301 and is preferably a push-button, instantaneous switch that connects the internal power source 310 to bougie lights 111, either directly or indirectly through electronics that are preferably housed in handle top 302. Handle top 302 generally contains plug 320, which powers lighted bougie 10 through its proximal end 130. A switch 321 may be included to allow for light intensity adjustments in bougie lights 111 and/or midline guidance light 322, which is also preferably mounted in handle top 302 and projected forward and downward toward the patient's neck. Midline guidance light 322 is preferably housed in nose 323 of handle top 302, though this is not a requirement of the invention. When handle 30 contains a midline guidance light 322, handle top 302 may contain a switch 324 to turn this light on or off depending on the clinical scenario. Also, to better match light intensity to ambient environment conditions, handle top 302 preferably contains an ambient light sensor 325, which can scale the circuit output to increase or decrease bougie light 111 and/or midline guidance light 322 intensity automatically. An indicator light 326 may also be included on handle top 302 to inform the user of device status. On the opposite end of handle 30 is handle bottom 303.

Figure 14:
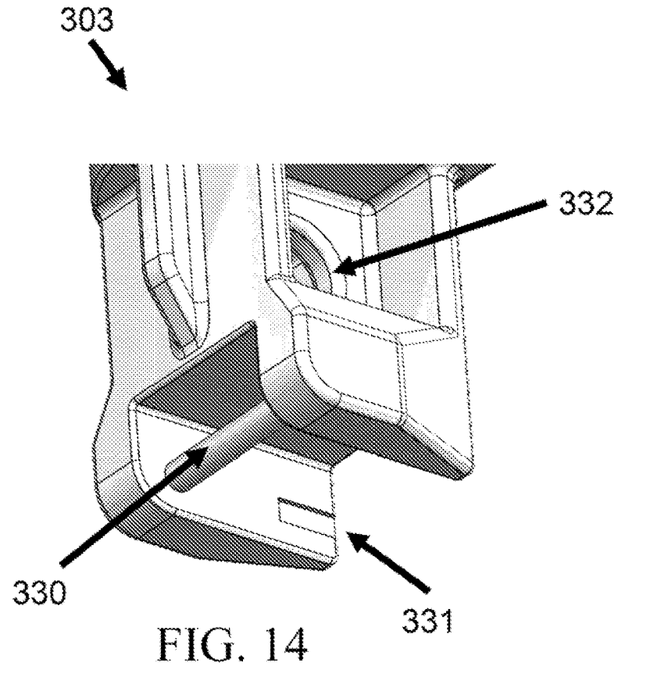
FIG. 14 shows a close-up view of the bottom section 303 of handle 30.

FIG. 14 shows a close-up view of the bottom section 303, which is preferably where intubating channel 20 is attached. In the preferred embodiment, the handle 30 and intubating channel 20 are separable and attach in a manner similar to conventional laryngoscopes. Handle bottom 303 generally has a post 330 around which hook 207 of intubating channel 20 can be placed, and slots 331, in which detents 208 of intubating channel 20 can be snapped into. The preferred embodiment of handle 30 also has a temporary docking hole 332 for the endotracheal tube adapter 62, which can be placed therein from either side and is generally held in place by friction. Note that an alternate embodiment of the intubation assistance system 1 may have intubating channel 20 and handle 30 connected as one, and not separable. In this instance, the connection is preferably pivotable such that intubating channel 20 can fold up alongside the body of handle 30 for more efficient packaging.

Figure 15:
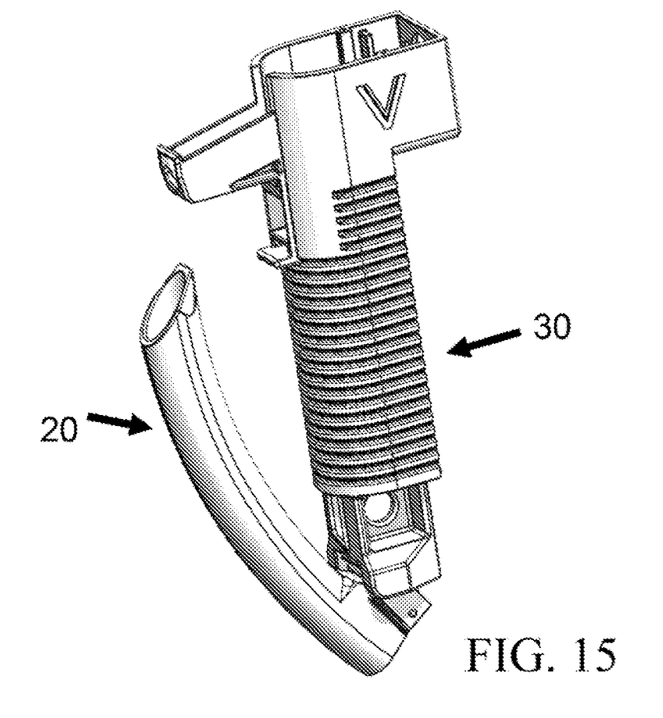
FIG. 15 shows an embodiment having intubating channel 20 and handle 30 connected as one.
Figure 16:
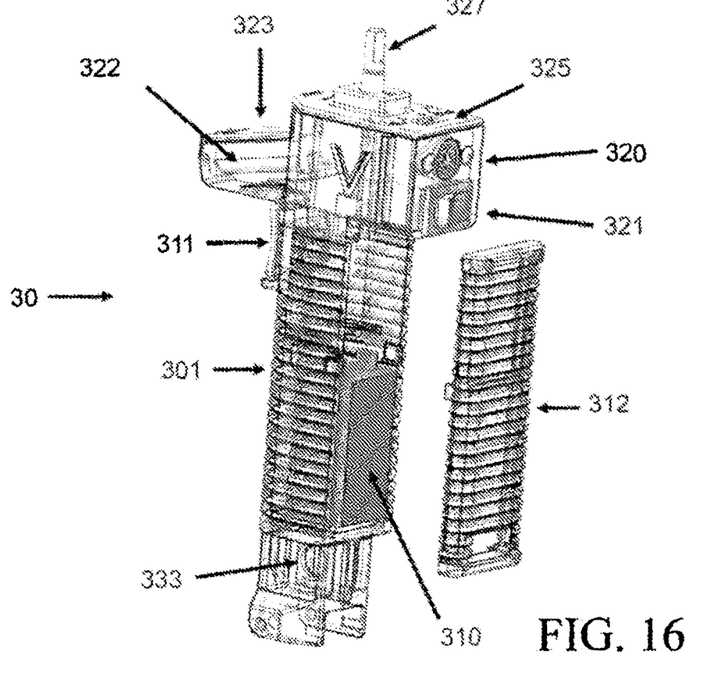
FIG. 16 shows an alternate embodiment of the handle 30.

FIG. 15 shows an example of this folding configuration with intubating channel 20 and handle 30 connected as one. An alternate embodiment of handle 30 is shown in FIG. 16. This embodiment allows the user more control of intensity in the bougie light 111 and/or midline guidance light 322 in the form of a rotary dial or knob 327 (e.g., rotary encoder, rheostat, etc.). Note that the embodiment of FIG. 13 preferably has a three-position switch 321 offering low, medium, and high intensity, which can be scaled additionally by ambient light sensor 325. The embodiment of FIG. 16 provides finer adjustment, possibly for a more skilled user with knob 327. Note that in the cases where power source 310 is removeable from handle 30, it may be removeable through a back panel 312.

Figures 17, 18:
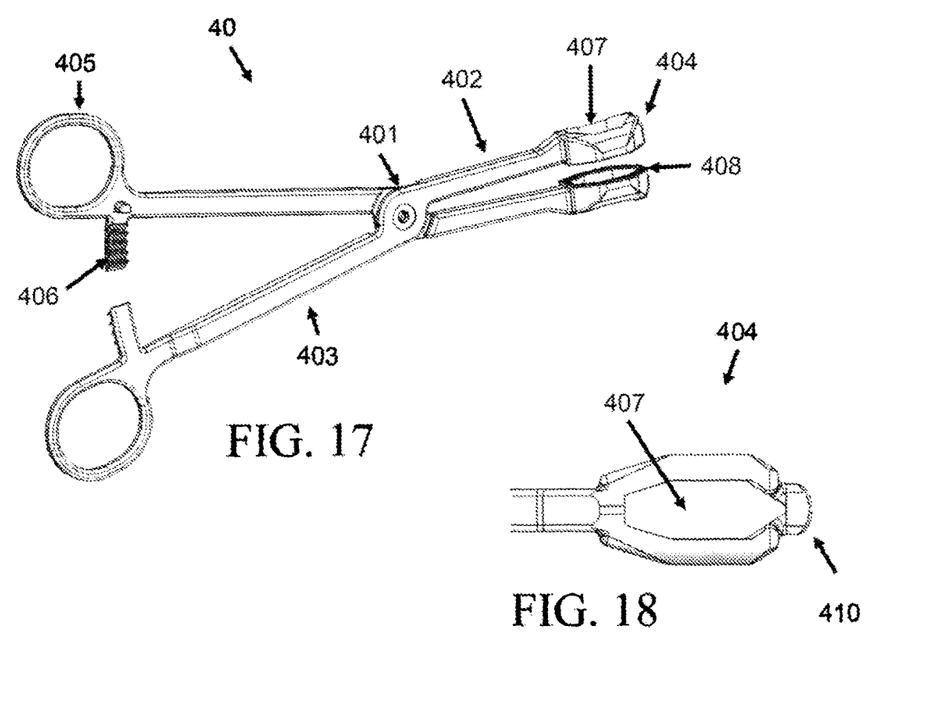
FIG. 17 is a detailed view of the tongue grasper 40.
FIG. 18 is a close-up view of an embodiment of grasping pad 404 of tongue grasper 40.

FIG. 17 shows a tongue grasper 40 of the preferred embodiment, which is constructed of two generally identical parts, held together at pivot point 401. Extending distally from pivot point 401 is distal extension 402, which terminates at grasping pad 404. Extending proximally from pivot point 401 is proximal extension 403, which terminates with finger loop 405. Also near finger loop 405 are locking teeth 406, which hold grasping pads 404 together. Grasping pads 404 are preferably ring-like structures with hollow openings 407 to allow tissue displacement and textured surfaces 408 to prevent slippage. FIG. 18 shows an alternate embodiment of tongue grasper 40, where grasping pad 404 is sized to fit inside proximal opening 203 of intubating channel 20 to facilitate endotracheal tube stabilization during the channel withdrawal step of the system procedure. Distal tip 410 of grasping pad 404 may also be shaped such that it better mates with the proximal end of endotracheal tube 60 for enhanced stabilization.

Having now fully set forth the preferred embodiments and certain modifications of the concept underlying the present invention, various other embodiments as well as certain variations and modifications thereto may obviously occur to those skilled in the art upon becoming familiar with the underlying concept. It is to be understood, therefore, that the invention may be practiced otherwise than as specifically set forth herein.

We claim:
1. An intubation system configured to facilitate placement of an endotracheal tube in a patient comprising:
 a tracheal introducer comprising an elongate flexible member sized for passing said endotracheal tube over, said tracheal introducer including at least one distal point source of light of a first color for directionally transilluminating to a surface of said patient's anterior neck;

an intubating channel comprising an elongate hollow member sized for internally passing said tracheal introducer and said endotracheal tube, said intubating channel being less flexible than said tracheal introducer and said endotracheal tube, for guiding said tracheal introducer and said endotracheal tube toward the vocal cords of said patient;

a handle attachable to said intubating channel for grasping and manipulating said intubating channel within said patient's mouth; and a power source in said handle and connected to said tracheal introducer for powering said at least one distal light on said tracheal introducer; and an external light mounted on said handle for projecting a linear reference onto the exterior of said patient's neck, said linear reference being a second color contrasting with said first color.

2. The intubation system of claim 1, wherein said at least one distal light is mounted at an acute angle relative to a center axis of said tracheal introducer for both axial and anterior radial transillumination.

3. The intubation system of claim 1, wherein said at least one distal light projects at least 20% of relative luminous intensity both axially and radially.

4. The intubation system of claim 1, further comprising an electronic circuit to control said at least one distal light.

5. The intubation system of claim 4, whereby said electronic circuit causes said at least one distal light to blink.

6. The intubation system of claim 4, whereby said electronic circuit causes said at least one distal light to dim or brighten.

7. The intubation system of claim 4, whereby said electronic circuit includes an intensity switch.

8. The intubation system of claim 4, further comprising a light sensor, whereby said electronic circuit adjusts the light intensity of said at least one distal light automatically based upon input from said sensor.

9. The intubation system of claim 8, whereby said light sensor is an ambient light sensor.

10. The intubation system of claim 4, wherein said handle contains said electronic circuit.

11. The intubation system of claim 1, wherein said handle is a detachable handle.

12. The intubation system of claim 11, wherein said handle contains said power source and said tracheal introducer comprises a plug configured to plug into said handle for powering said at least one distal light on said tracheal introducer.

13. The intubation system of claim 1, wherein said handle further comprises a dock for docking said tracheal introducer.

14. The intubation system of claim 1, wherein said tracheal introducer comprises an electrical connector for connecting said power source.

15. The intubation system of claim 1, wherein said intubating channel is a curved hollow structure with malleability.

16. The intubation system of claim 1, whereby said intubating channel is tubular.

17. The intubation system of claim 1, whereby said intubating channel includes a ventilation port.

18. The intubation system of claim 1, wherein said intubating channel projects substantially at 90 degrees from said handle.

19. The intubation system of claim 1, further comprising graspers for manipulating the tongue of said patient.

20. The intubation system of claim 1, whereby said external light is a laser.

21. The intubation system of claim 1, further comprising electrical conductors connecting said at least one distal light to said power source.

22. The intubation system of claim 21, wherein said electrical conductors are embedded in said tracheal introducer.

23. The intubation system of claim 21, whereby said tracheal introducer is partially formed of electrically conductive material to define said electrical conductors.

24. The intubation system of claim 1, wherein said intubating channel is curved anteriorly with respect to said patient's anatomy.

25. The intubation system of claim 1, wherein said intubating channel is constructed of more than one material.

26. The intubation system of claim 1, wherein said handle further comprises an elongate housing configured for hand-grasping, and a switch mounted on said housing and configured for finger activation while said handle is grasped in a user's hand.

* * * * *